(12) United States Patent
Bare et al.

(10) Patent No.: US 12,330,172 B2
(45) Date of Patent: *Jun. 17, 2025

(54) METHOD OF USE OF CELLULAR COMPONENT CONCENTRATOR AND FILTER APPARATUS

(71) Applicant: ARTHREX, INC., Naples, FL (US)

(72) Inventors: Christopher M. Bare, Naples, FL (US); Robert M. Harrison, IV, Naples, FL (US); Melissa S. Tucker, Estero, FL (US); Abigail Nabors, Naples, FL (US)

(73) Assignee: Arthrex, Inc., Naples, FL (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/947,664

(22) Filed: Sep. 19, 2022

(65) Prior Publication Data
US 2023/0018329 A1     Jan. 19, 2023

Related U.S. Application Data (63) Continuation of application No. 15/554,889, filed as application No. PCT/US2016/021699 on Mar. 10, 2016, now Pat. No. 11,534,774.

(60) Provisional application No. 62/131,045, filed on Mar. 10, 2015.

(51) Int. Cl.
| | |
|---|---|
| *B04B 7/18* | (2006.01) |
| *A61K 35/14* | (2015.01) |
| *B01L 3/00* | (2006.01) |
| *B04B 3/08* | (2006.01) |

(Continued)

(52) U.S. Cl.
CPC ............. *B04B 7/18* (2013.01); *A61K 35/14* (2013.01); *B01L 3/502* (2013.01); *B04B 3/08* (2013.01); *B04B 5/10* (2013.01); *B04B 11/04* (2013.01); *B01L 2300/0681* (2013.01); *B01L 2300/0803* (2013.01); *B01L 2400/0409* (2013.01)

(58) Field of Classification Search
CPC .... B04B 7/18; B04B 3/08; B04B 5/10; B04B 11/04; A61K 35/14; B01L 3/502; B01L 2300/0681; B01L 2300/0803; B01L 2400/0409
USPC ....................................... 424/94.64
See application file for complete search history.

(56) References Cited

U.S. PATENT DOCUMENTS

| | | | |
|---|---|---|---|
| 4,647,376 A * | 3/1987 | Galaj | G01N 1/4077 210/257.2 |
| 5,601,711 A | 2/1997 | Sklar et al. | |
| 5,922,288 A | 7/1999 | Herst | |

(Continued)

FOREIGN PATENT DOCUMENTS

| | | |
|---|---|---|
| WO | WO 2014/127250 A1 | 8/2014 |

OTHER PUBLICATIONS

Chen et al., "Rare cells detection by selective enrichment with a novel multilayer concentric filter device", The 9th IEEE International Conference on Nano/Micro Engineered and Molecular Systems (NEMS), IEEE, Apr. 13-16, 2014, pp. 407-410.

(Continued)

*Primary Examiner* — Hayden Brewster
(74) *Attorney, Agent, or Firm* — Lathrop GPM LLP; Lisa Hillman (57) ABSTRACT

The present disclosure describes a disc-like apparatus and method of its use allowing for the one-step concentration and separation of therapeutic factors found in mammalian body fluid.

19 Claims, 4 Drawing Sheets

(51) Int. Cl.
B04B 5/10 (2006.01)
B04B 11/04 (2006.01)

(56) References Cited

U.S. PATENT DOCUMENTS

| | | | |
|---|---|---|---|
| 6,309,362 B1* | 10/2001 | Guirguis | G01N 1/312 |
| | | | 422/63 |
| 10,012,640 B2 | 7/2018 | Pant et al. | |
| 10,202,569 B2 | 2/2019 | Novak et al. | |
| 2005/0170515 A1 | 8/2005 | Moore | |
| 2007/0224591 A1 | 9/2007 | Gui et al. | |
| 2008/0210645 A1 | 9/2008 | Coull et al. | |
| 2009/0050565 A1 | 2/2009 | Muralidhara et al. | |
| 2010/0206798 A1* | 8/2010 | Dorian | A61M 1/3679 |
| | | | 210/267 |
| 2011/0120959 A1* | 5/2011 | Levitt | B01D 21/2411 |
| | | | 210/304 |
| 2012/0003675 A1 | 1/2012 | Retterer et al. | |
| 2012/0226218 A1 | 9/2012 | Phillips et al. | |
| 2012/0231529 A1* | 9/2012 | Kyle | C12M 45/04 |
| | | | 210/232 |
| 2012/0261326 A1* | 10/2012 | Deschamps | B01D 35/30 |
| | | | 210/236 |
| 2014/0045249 A1 | 2/2014 | Yao et al. | |
| 2016/0000886 A1 | 1/2016 | Parker et al. | |

OTHER PUBLICATIONS

Chen et al., "A multilayer concentric filter device to diminish clogging for separation of particles and microalgae based on size", Lab Chip., Apr. 21, 2014, 14(8): 1459-1468.

International Search Report and Written Opinion for corresponding PCT Application No. PCT/US2016/021699, dated May 12, 2016.

Millipore, "Product Selection Guide, Ultrafiltration Membranes," 2008, accessed on the Internet at http://wolfson.huji.ac.il/purification/PDF/dialysis/MILLIPOREUltrafiltrationMernbranes.pdf on Jan. 9, 2020, 4 pages.

U.S. Appl. No. 15/554,889 2018/0043375 U.S. Pat. No. 11,534,774, filed Aug. 31, 2017 Feb. 15, 2018 Dec. 27, 2022, Christopher M. Bare, Cellular Component Concentrator and Filter Apparatus and Method of Use Thereof.

U.S. Appl. No. 17/947,664 2023/0018329, filed Sep. 19, 2022 Jan. 19, 2023, Christopher M. Bare, Cellular Component Concentrator and Filter Apparatus.

* cited by examiner

METHOD OF USE OF CELLULAR COMPONENT CONCENTRATOR AND FILTER APPARATUS

CROSS-REFERENCE TO RELATED APPLICATIONS

This application is a continuation of U.S. patent application Ser. No. 15/554,889, filed Aug. 31, 2017, which is a 35 U.S.C. § 371 national phase entry of PCT/US2016/021699, filed on Mar. 10, 2016, which claims the benefit of U.S. Provisional Application No. 62/131,045, filed Mar. 10, 2015, which are incorporated herein in their entireties.

BACKGROUND

This disclosure relates to apparatus and methods for isolating and concentrating therapeutically active factors from mammalian body fluids.

Systems and methods of producing therapeutic fluid and compositions with enhanced concentrations of therapeutically active factors can be used in the treatment of mammalian injuries or diseases.

SUMMARY

Therapeutic factors, including growth factors, cytokines, and certain proteins, are known to be useful for treating damaged mammalian tissue. Therapeutic factors can be found in mammalian fluids. These therapeutic factors can be concentrated by methods known in the art. However, these methods require multiple steps or devices, are time consuming, and inefficient. There is thus a need for less demanding methods for expanding, concentrating, and isolating therapeutic factors.

A disc-like apparatus and methods of its use are disclosed herein for allowing for the one-step concentration and separation of therapeutic factors found in a mammalian body fluid. Advantageously, the apparatus and methods of use can also expand or increase the amount of therapeutic factors in therapeutic fluid.

The apparatus comprises a disc-like shape: a top plate comprising an inner and outer surface, a bottom plate comprising an inner and outer surface, an outside wall with an inner and outer surface, a compartment enclosed by the inner surface of the top plate, the inner surface of the bottom plate, and the inner surface of the outside wall, and at least one porous filter element or membrane located inside of the compartment.

Disclosed herein are methods of producing a therapeutic fluid from mammalian body fluid with an increased concentration of therapeutic factors, including, but not limited to anabolic growth factors, cytokines, and proteins. A method comprises the steps of obtaining mammalian body fluid and injecting a portion of the body fluid into the apparatus, centrifuging the body fluid in the apparatus, and removing the effluent, which is a therapeutic fluid enriched with therapeutic factors. The method can also include expanding or increasing the amount of therapeutic factors in therapeutic fluids.

DETAILED DESCRIPTION

The use of recombinant therapeutic factors in the treatment of mammalian wounds and disease has been practiced in the medical arts. Autologous proteins that are intrinsic to the body are advantageous in patient treatment due to, inter alia, the natural post-translational modifications that are already present at the time of collection. These post-translational modifications are often lacking in recombinant proteins.

Body fluids or tissues can be collected from a mammal, optionally expanded, concentrated, and isolated, using the compositions and methods disclosed herein. The resulting therapeutic fluid can be used to therapeutically treat humans and other mammals.

The present disclosure is directed to the expansion, concentration, and filtration of mammalian body fluids using a single concentrator apparatus and uses of the therapeutic fluid produced by the apparatus.

Apparatus.

The disclosed concentrator apparatus 110 is in a disc-like shape and primarily includes a top plate 1 comprising an inner 10 and outer surface 5, a bottom plate 15 comprising an inner 25 and outer surface 20, a center or central area 45, an outside wall 30 with an inner surface 40 and outer surface 35, a compartment 65 enclosed by the inner surface 10 of the top plate 1, the inner surface 25 of the bottom plate 15, and the inner surface 40 of the outside wall 30, and at least one porous filter element or membrane 50 located inside of the compartment 65. The outer surfaces of the top plate 1, bottom plate 15, and outside wall 30 are exposed to the outside environment and define the outer boundaries of the apparatus 110. The height of the outside wall 30 of the apparatus defines the height of the apparatus. The height of the apparatus can be dependent upon the centrifuge with which the apparatus is used. The height of the apparatus can also be dependent on the physical strength of the filter element or membrane being used. The device can have a height range of substantially 15 mm to substantially 200 mm. The apparatus can have a diameter ranging from substantially 100 mm to substantially 800 mm.

Inside the compartment, the at least one filter element or membrane can comprise an inside edge 51 and an outside edge 52. A body fluid reservoir 70 can be present in the compartment and can be surrounded by the inside edge 51 of the at least one filter element or membrane. A therapeutic fluid reservoir 75 can be present in the compartment and located between the outside edge 52 of the at least one filter element or membrane and the inner surface 40 of the outside wall 30. Therefore, the at least one filter element or membrane 50 can separate the compartment 65 into at least one body fluid reservoir 70 and at least one therapeutic fluid reservoir 75. The body fluid reservoir can encompasses the central area 45 of the apparatus.

The disc-like shape of the apparatus enables the use of cross-flow and direct flow filtration in a single device. Cross-flow filtration allows the body fluid to pass along the surface of the filter tangentially. The pressure difference across the filter drives components that are smaller than the filter pores through the filter. Direct flow filtration is the filtration technique where the body fluid passes directly through the filter instead of traveling tangentially along the filter. The apparatus permits body fluids containing therapeutic factors to be concentrated and filtered in a single device. Advantageously, the therapeutic factors can be expanded or increased in amount using the compositions and methods disclosed herein. The compositions and methods of the present disclosure provide therapeutic fluid for treating diseased, wounded, or damaged mammalian tissue.

The apparatus can be formed of materials such as plastics, including but not limited to, polyolefins, polystyrene, polyallomer, polypropylene, polyvinyl chloride, polyethylene terephalate glycol modified, and polycarbonate. A device can be sterilized and should be able to tolerate the sterilization processes as known in the art. The device will also be subject to centrifugation and must tolerate a centrifugation protocol.

Figure 8:
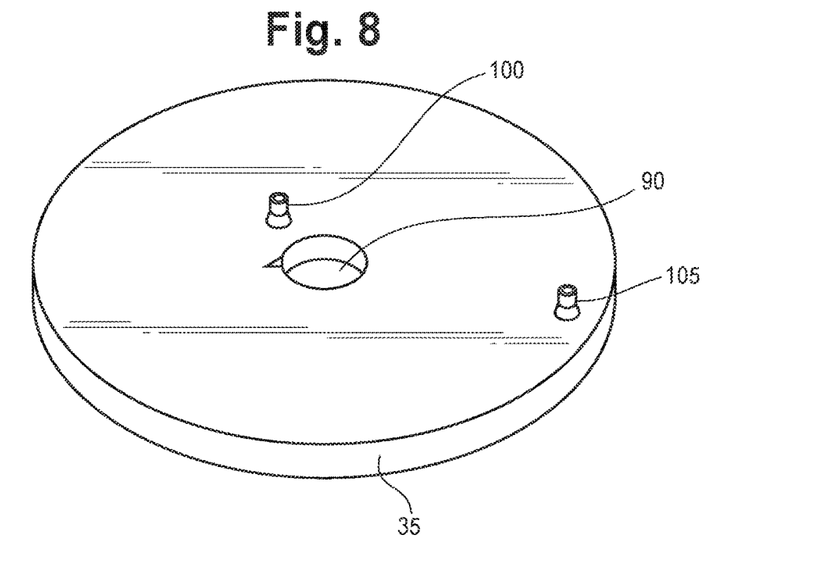
FIG. 8. Shows an apparatus where the apparatus attaches to a centrifuge spindle by way of the attachment point in the center of the apparatus.

The device can rotate around an axis of rotation through the center of the device and perpendicular to the top plate 1 and bottom plate 15. The device can comprise components allowing for the device to attach to a rotor in any type of laboratory or industrial centrifuge. The device can comprise attachment points 80 on the outside wall 30 of the disc where the centrifuge rotor makes contact with the outer surface 35 of the outside wall 30 of the device. These attachment points 80 can be in the form of notches 85, fingers, gear teeth, or cogs. The sizes and shapes of the notches 85, fingers, gear teeth, and cogs can depend on the centrifuge and the shape of the centrifuge rotor. The device can act as a rotor in a laboratory centrifuge. The device can comprise an attachment point 90 to the centrifuge in the center of the disc-like apparatus. The apparatus can comprise a hole in the center allowing for the apparatus to attach to the spindle of a centrifuge.

Figure 1:
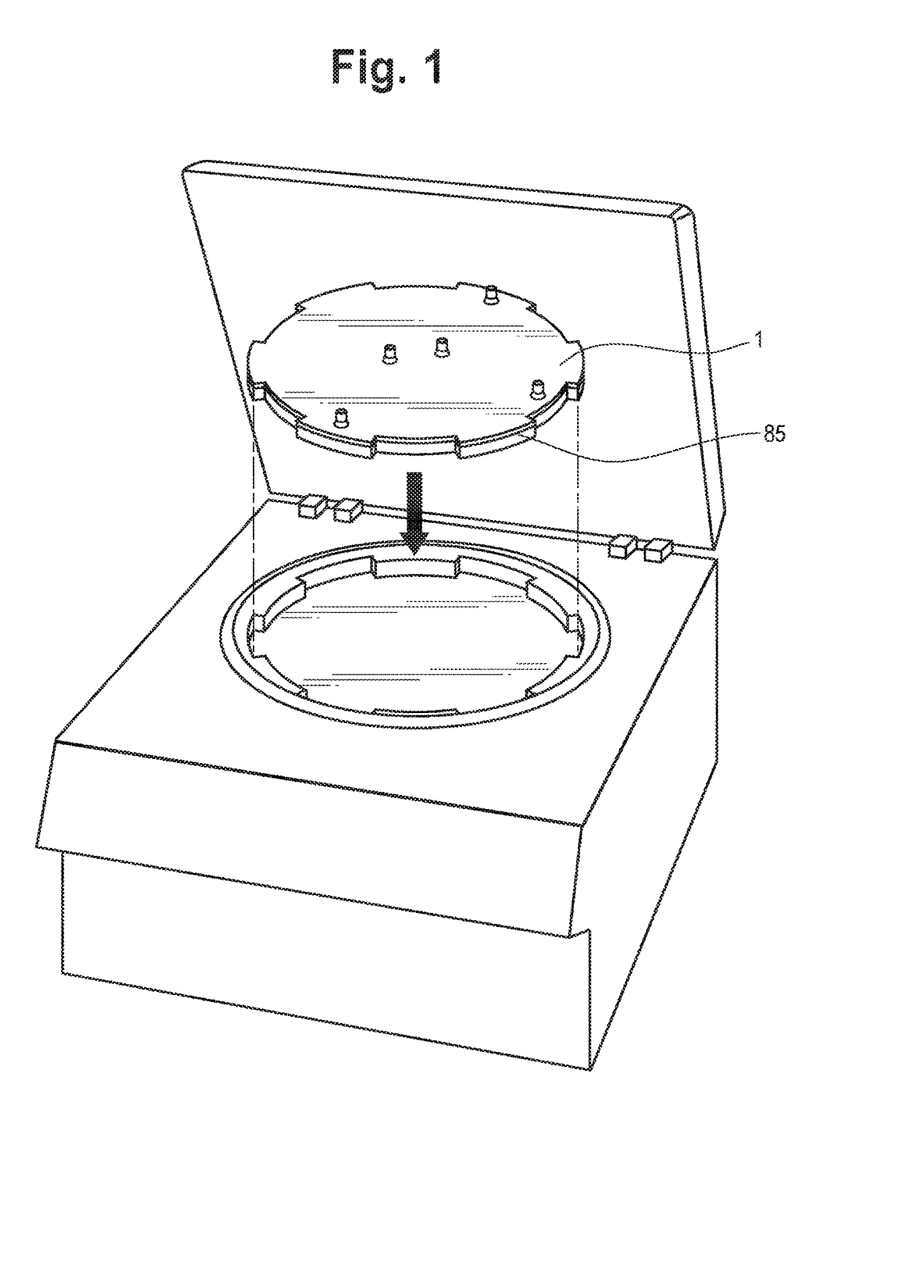
FIG. 1. Represents a composition entering a centrifuge.
Figure 2:
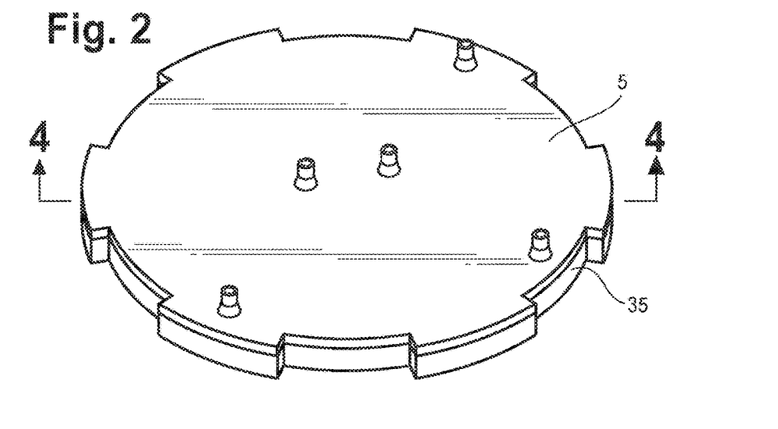
FIG. 2. Shows a top-view of an apparatus.
Figure 3:
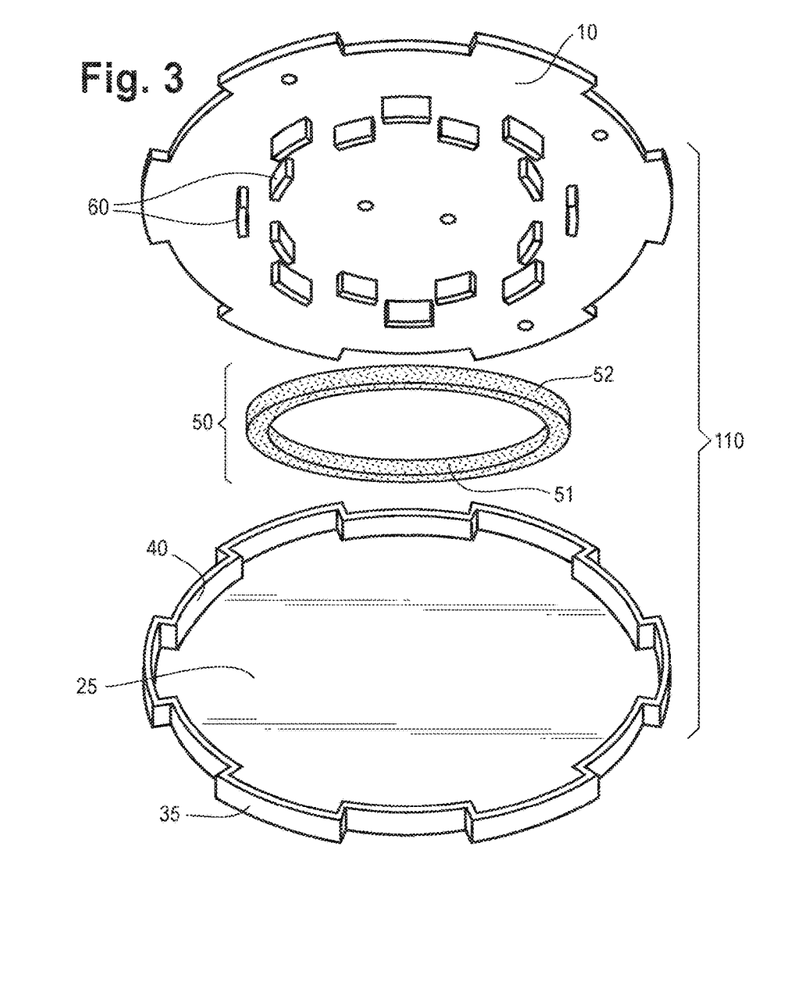
FIG. 3. Shows an apparatus in an opened state showing the top plate, a filter element, and the outside wall attached to the bottom plate.
Figure 4:
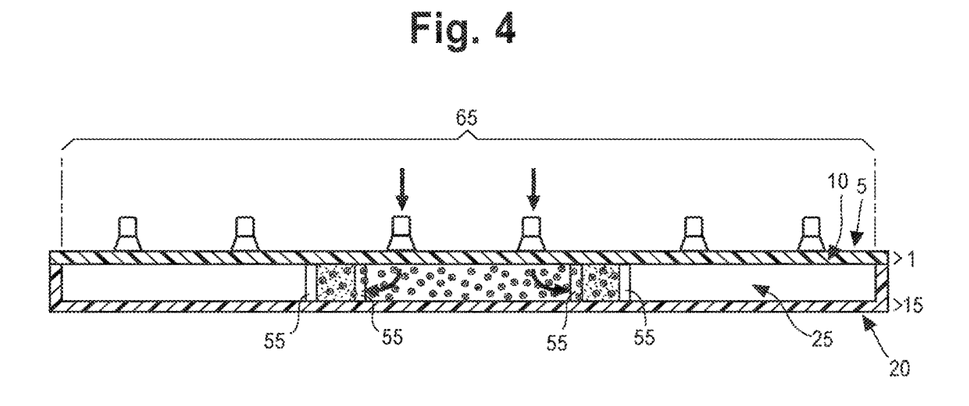
FIG. 4. Represents a cross-section of an apparatus as in FIG. 2 showing ports where body fluid is added to the body fluid reservoir and the flow of body fluid through the filter element or membrane of the apparatus while centrifuging.
Figure 5:
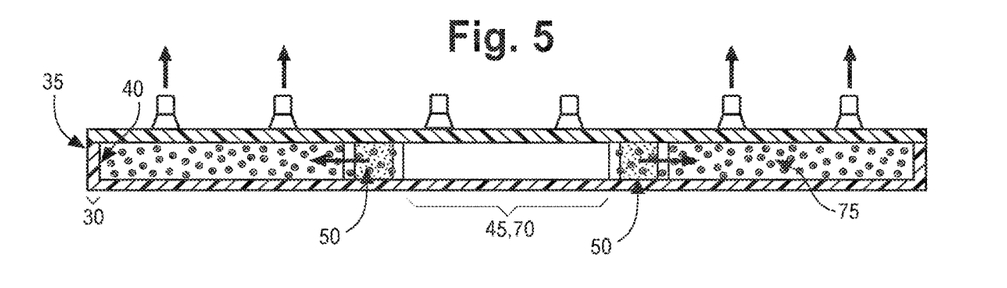
FIG. 5. Represents a cross-section of an apparatus as in FIG. 2 after centrifugation showing the therapeutic fluid located in the therapeutic fluid reservoir, the ports to remove the therapeutic fluid, and some of the filtered items remaining in the filter element.

The top plate 1 and the bottom plate 15 can be permanently fused to the outside wall 30, all three together creating a one-piece disc. The top plate and bottom plate can be separable and allow for the two-piece disc to be opened, see FIG. 3. The outside wall 30 can be permanently attached or detachable from the top plate or bottom plate. Optionally, a portion of the outside wall can be permanently attached to the both the top and bottom plates and the portions of the outside walls fit together (permanently or detachably) to make the whole outside wall. The opening of the two-piece disc enables components on the inside of the apparatus to be changed. These components can include filter elements or membranes 50, scaffolding devices 95, and the like. The entire device, filter elements or membranes, scaffold device, or combinations thereof can be disposable.

Figure 6:
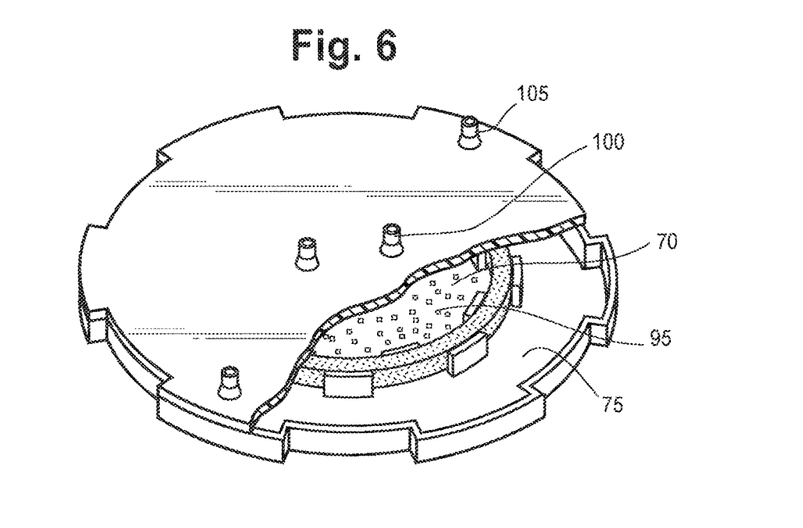
FIG. 6. Represents a cutaway view of an apparatus depicting the filter element or membrane, the filter element or membrane holders, the body fluid reservoir, the therapeutic fluid reservoir, and scaffolding in the body fluid reservoir.
Figure 7:
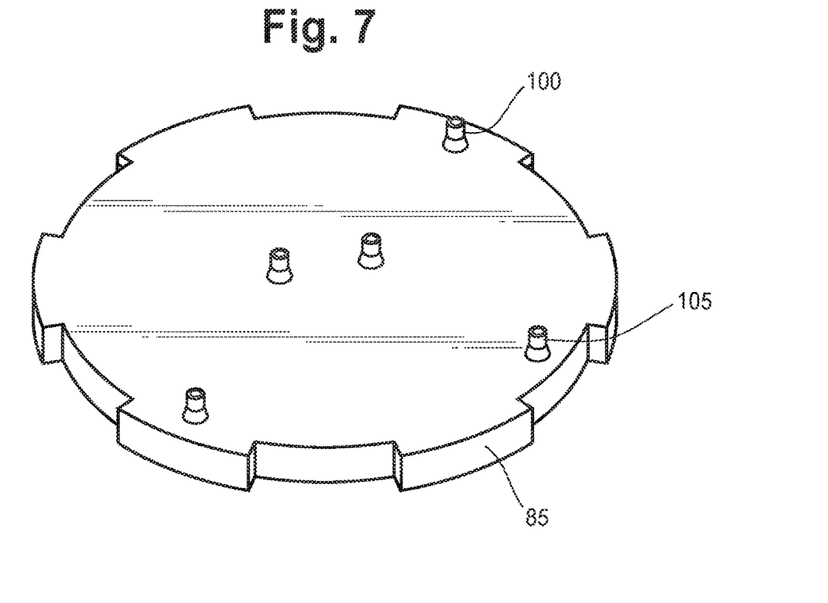
FIG. 7. Shows a top-view of an apparatus.

Devices can comprise a filter element or membrane fastener or holder 55 on the inner surface of the top plate 10 or the inner surface of the bottom plate 25, or on both inner surfaces. The fastener or holder anchors the filter element or membrane 50 in place. The filter element or membrane can be positioned so that the filter element separates the compartment 65 enclosed by the inner surface of the top plate 10, the inner surface of the bottom plate 25, and the inner surface of the outside wall 30 of the apparatus. The filter element or membrane separates the compartment so that the device comprises a pre-membrane compartment, or body fluid reservoir 70, and a post-membrane compartment, or therapeutic fluid reservoir 75. The body fluid reservoir encompasses the central area 45 and can be surrounded by the filter element or membrane 50. The therapeutic fluid reservoir 75 can be located between the filter element or membrane and the inner surface 40 of the outside wall 30 of the apparatus. The fastener or holder can comprise struts 60 that extend into the compartment enclosed by the inner surface of the top plate, the inner surface of the bottom plate, and the inner surface of the outside wall of the apparatus. The struts 60 act to hold the filter element or membrane in place. The struts allow for the weaving or attachment of the filter element or membrane, securing the filter element or membrane in place.

The central area 45 area can comprise the body fluid reservoir, or can comprise the body fluid reservoir as well as a center centrifuge attachment point 90. The body fluid reservoir can be donut shaped surrounding the open center centrifuge attachment point.

The filter element or membrane 50 can be in a circular shape (FIG. 3), which is continuous so that the filter element or membrane encircles the body fluid reservoir 70. With the body fluid reservoir encircled by the filter element or membrane, the body fluid placed into the body fluid reservoir is ensured to pass through the filter element or membrane. A filter element or membrane can span the height of the entire compartment such that one edge of the filter element is in contact with the inner surface of the top plate, and one edge of the filter element is in contact with the inner surface of the bottom plate, ensuring that the body fluid passes through the filter or membrane element.

The filter element or membrane can be embedded within the apparatus. For example, the filter element or membrane can be attached to the inner surface of the top plate, bottom plate, or the top and bottom plates.

The filter element or membrane can filter out, for example, cells, tissue, growth factors, cytokines, proteins, and debris from the body fluid.

The body fluid reservoir 70 can be empty until the body fluid is placed inside of the reservoir. The fluid reservoir can also comprise a scaffolding device 95. The scaffolding device can be comprised of any one, or a combination, of the following: a plurality of beads, spheres, gels, wool, powder, granules, particles, autograft, allograft, or xenograft mammalian bone, and/or mammalian tissue including, but not limited to, muscle, cartilage, tendon, vascular tissue, organ tissue, and the like. The beads, spheres, gels, wool, powder, granules, and particles can be made of, for example, glass, plastic, corundum, and/or quartz. The surface area of the scaffolding device can be increased by etching the surface of the beads, spheres, granules, and particles through methods known in the art. The scaffolding device can be held in place by a housing, such as a cassette or holder. Such a housing could comprise the same type of material as the scaffolding device, glass, plastic, corundum, and/or quartz, or any combination. The scaffolding can also be loose in the body fluid reservoir. The scaffolding device can be the inner surface of the top plate and/or the inner surface of the bottom plate and comprise etches, ribs, or ridges on these surfaces.

The scaffolding device can comprise a combination of any of the following: a plurality of beads, spheres, gels, wool, powder, granules, particles, mammalian tissue, and/or mammalian bone, and etches, ribs, ridges, and/or the like on the inner surface of the top plate and/or the inner surface of the bottom plate.

The scaffolding device increases solid surfaces exposed to the body fluid. The higher surface area allows cells in the body fluid to attach to the scaffolding. Once attached, the cells can produce therapeutic factors. In one example, monocytes can adhere to the scaffolding device. The attachment of monocytes stimulates monocyte production of therapeutic factors, for example but not limited to, IL-1ra, fibrinogen, thrombin, and alpha-2-macroglobulin. In another example, thrombocytes attach to the scaffold device and stimulate production of therapeutic factors such as platelet derived growth factor (PDGF). The body fluid can be derived from mammalian tissue, such as but not limited to, liver, cartilage, bone, muscle, and the like. Additionally, the body fluid can comprise cells derived from mammalian liver. These cells can adhere to the scaffold device and produce fibrinogen and thrombin.

Therefore, a device not only filters and concentrates therapeutic factors, but it also can expand or multiply the amount of therapeutic factors such that there are more therapeutic factors in the therapeutic fluid than were present in the bodily fluid. The therapeutic fluid can comprise 5, 10, 15, 20, 30, 40, 50, 60, 70, 80, 90% or more therapeutic factors than were present in the starting bodily fluid. The therapeutic fluid can contain 0.5, 1, 2, 3, 5, 10 or more times the amount of therapeutic factors in the therapeutic fluid than were present in the starting bodily fluid.

The top or bottom plate can comprise at least one body reservoir port 100 located in the fluid reservoir. The at least one port in body the fluid reservoir allows for the placement of body fluid into the fluid reservoir. The top or bottom plate can also comprise at least one therapeutic reservoir port 105 located in the therapeutic fluid reservoir. The at least one port in the therapeutic fluid reservoir allows for removal of therapeutic fluid from the device. These ports can be capped with a capping device as to seal (i.e., a sealing element) the apparatus. These capping devices can be Leur Locks, or any other cap that attaches to, and seals the port.

A filter element or membrane can comprise a packed bed matrix. A packed bed is a bed of granular material which retains the solid particles as the body fluid passes through the matrix, allowing fluids and liquids to be filtered free of solid contaminants or components. The granular material for the packed bed can be sand, although celite or diatomaceous earth packed in a microscale container can also serve as the packed bed. Incompressible diatomaceous earth (i.e. primarily silica), wood cellulose or other inert porous solids can also be used as the granular material of the packed bed filter. A packed bed matrix can be used as the filtration element of the concentrator device such that when the body fluid is passed through the matrix, solid components or fluid components with a size greater than the pore size of the packed bed material can be retained on the packed bed, while other fluid components pass through. A packed bed matrix can be contained in a housing comprising a circular shape which encircles the fluid reservoir. The housing provides a barrier to keep the packed bed matrix in place and with the proper pore size.

The filter element or membrane can comprise a network of one or more nanofibers, a nanofibrillar structure, glass, silicon, zinc, silver, or plastic comprising an etched or micropatterned surface, glass, silicon, or plastic surface comprising macropores or nanopores, a polymer scaffold, polyethersulfone (PES), modified PES, polyvinylidene fluoride (PVDF), mixed cellulose esters, other polymeric membranes, or the like.

The filter element or membrane can comprise pores ranging from substantially 5 kD to substantially 0.6 microns. The apparatus can comprise filter elements or membranes comprising pore sizes in the range including, but not limited to, 5, 10, 25, 50, 100, 200, 300, 400, 500, 600, 700, 800, 900, and 1,000 kD as well as, 0.2, 0.3, 0.45 microns, and larger.

The apparatus can comprise more than one filter element or membrane fastener or holder 55 on the inner surface of the top plate, the inner surface of the bottom plate, or on the inner surfaces of the top and bottom plates. More than one filter element or membrane can be present in the devices. Every filter element or membrane can comprise a same or different pore size from the other filter elements or membranes of the apparatus. Where an apparatus comprises more than one filter, the number of filters can be dependent on the size of the apparatus, the size of the target therapeutic factor, the volume of body fluid placed in the fluid reservoir, or combinations thereof. The volume of fluid can decrease as it passes through one or more filters. In one example, in a multifilter apparatus, the filter closest to the center of the apparatus can comprise one size of pores that can be of a larger size than the pores of the filter closest to the outside wall of the apparatus. In a non-limiting example, the filter closest to the center of the apparatus can comprise pores that are 0.45 microns while the filter closest to the outside wall of the apparatus can comprise pores of 0.22 microns.

Methods of Use of Devices.

Devices disclosed herein can be used to filter body fluids, concentrate body fluids and therapeutic factors, expand the amount of therapeutic factors, or combinations thereof. Body fluid from a patient can be placed into a body fluid reservoir 70 of a device. The amount of body fluid can be placed into the body fluid reservoir can be dependent on the size of the device, which can be dependent on the size of centrifuge being used. Capacity for body fluid of the apparatus largely depends on the size of the apparatus as well as the amount of scaffolding device added to the body fluid reservoir. Devices can hold a range of fluid volumes, including but not limited to substantially 10, 25, 50, 75, 100, 125, 150, 180, 200, 250, 300, 500, 1,000, 2,000, 3,000, 4,000, 5,000, 6,000, 7,000, 8,000, 9,000, 10,000, 11,000, 12,000 mL or more. In some examples, the apparatus can hold up to substantially 180 mL of fluid in the body fluid reservoir, substantially 525 mL of mammalian body fluid in the fluid reservoir, or substantially 12 L of mammalian body fluid in the fluid reservoir. The body fluid can be placed into the fluid reservoir through a port that opens to the fluid reservoir. Once the fluid is added to the fluid reservoir, a cap can be placed on the port so that the device is sealed.

A device can be filled with mammalian body fluid and immediately placed into a centrifuge. The device can be placed into a centrifuge and centrifuged for a sufficient time and at a sufficient gravitational force to allow for separation and filtration of the fluid and components without denaturation of the proteins. In one example, the sufficient gravitational force occurs in the range of substantially 1×g to 600,000×g, including, but not limited to 1,000, 2,500, 5,000, 10,000, 12,500, 15,000, 20,000, 25,000, 30,000, 35,000, 40,000, 50,000, 60,000, 70,000, 80,000, 90,000, 100,000, 125,000, 150,000, 175,000, 200,000, 225,000, 250,000, 275,000, 300,000, 325,000, 350,000, 375,000, 400,000, 425,000, 450,000, 475,000, 500,000, 550,000, or 600,000×g. In another example, the sufficient time occurs in the range from substantially 1 minute to substantially 60 minutes, including but not limited to, 2, 5, 7.5, 10, 12, 15, 20, 25, 30, 40, 50, or 60 minutes. The centrifugation can occur in a temperature range of substantially 2° C. to ambient temperature, including, but not limited to, 2, 3, 4, 5, 6, 10, 15, 18, 19, 20, 21, or 22° C. At the conclusion of centrifugation, the device is carefully removed from the centrifuge. The cap covering the port for the therapeutic fluid reservoir can be removed and the therapeutic fluid removed from the device. The therapeutic fluid can then be administered to a patient or frozen for future therapeutic use.

The body fluid reservoir can comprise a scaffolding device 95, for example, autograft, allograft, or xenograft tissue or material. The scaffolding device can be loaded into the concentrator device through a port in the fluid reservoir or by separating the top plate from the bottom plate, placing the scaffolding device in the fluid reservoir, and reconnecting the top plate and bottom plate. Body fluid collected from a mammal can then loaded into the concentrator device through a port in the body fluid reservoir and the port can be sealed. The loaded concentrator device can then be placed in an incubator for a sufficient time and at a sufficient temperature to allow for production of the therapeutic factors by cells in the body fluid. In one example, this sufficient time can be in the range of 0 hours to substantially 72 hours including but not limited to, 0.5, 1, 2, 4, 6, 8, 12, 16, 20, 24, 32, 40, 48, 56, 64, or 72 hours.

There is a maximum time for incubation as the generation of anabolic factors begins to taper and slow, while the generation of catabolic factors begins and increases. With the slowing of the anabolic factors and the building of the catabolic factors, the ratio of anabolic to catabolic factors begins to decrease, decreasing the beneficial effect of the concentrated therapeutic fluid. Incubation temperatures can be in the range of substantially 20° C. to substantially 44° C., including but not limited to, 20, 24, 28, 32, 34, 35, 36, 37, 38, 39, 40, 42, or 44° C. At the end of the incubation, the device can be placed into a centrifuge and centrifuged for a sufficient time and at a sufficient gravitational force to allow for separation and filtration of the fluid and components without denaturation of the proteins. The sufficient gravitational force can occur in the range of substantially 1×g to 600,000×g, including, but not limited to 1,000, 2,500, 5,000, 10,000, 12,500, 15,000, 20,000, 25,000, 30,000, 35,000, 40,000, 50,000, 60,000, 70,000, 80,000, 90,000, 100,000, 125,000, 150,000, 175,000, 200,000, 225,000, 250,000, 275,000, 300,000, 325,000, 350,000, 375,000, 400,000, 425,000, 450,000, 475,000, 500,000, 550,000, or 600,000×g. In one example, the sufficient time occurs in the range from substantially 1 minute to substantially 60 minutes, including but not limited to, 2, 5, 7.5, 10, 12, 15, 20, 25, 30, 40, 50, or 60 minutes. The centrifugation can occur in a temperature range of substantially 2° C. to ambient temperature, including, but not limited to, 2, 3, 4, 5, 6, 10, 15, 18, 19, 20, 21, or 22° C. After completion of centrifugation, the device can be carefully removed from the centrifuge, the cap covering the port for the therapeutic fluid reservoir removed, and the therapeutic fluid removed from the device.

The therapeutic fluid can then be administered to a patient or chilled for future therapeutic use. The therapeutic fluid can be frozen at substantially −20° C. or below, or refrigerated at substantially 6° C. to substantially −20° C. Patient administration of the therapeutic fluid can include, for example, injection into a surgical site, injection into a damaged joint, injection to a damaged tissue, and the like. The methods can enrich the therapeutic fluid with Interleukin-1 receptor antagonist (IL-1ra), a cytokine possessing anabolic effects. IL-1ra binds to the interleukin-1ß (IL-1ß) receptor on cell surfaces, inhibiting the catabolic effect of IL-1ß. In one example, the methods can result in therapeutic fluid enriched with fibrinogen, thrombin, or both fibrinogen and thrombin. After the fibrinogen, thrombin, or both are recovered from the apparatus, they can be mixed with platelet rich plasma (PRP) or bone marrow concentrate (BMC) before patient administration.

One or more fluid fractions collected from the concentrator apparatus can correspond to concentrated body fluids. Various concentrated body fluids can be prepared by centrifugation or gravitational weight separation including, without limitation, whole blood, bone marrow, blood fractions (platelet rich plasma (PRP), platelet poor plasma (PPP)), stem cells (cord blood-derived and bone marrow-derived), concentrated seminal fluid, concentrated spinal fluid and the like.

The methods and devices disclosed herein can provide a concentration ratio of anabolic therapeutic factors to catabolic fluid components in a range of substantially 10:1 to substantially 1,000:1. Methods disclosed herein can provide a therapeutic fluid with substantially 10 to 80% of the initial body fluid volume. The range in volume of therapeutic fluid can be, but is not limited to, 10, 12, 14, 16, 18, 20, 22, 25, 27, 30, 34, 37, 40, 43, 47, 50, 53, 57, 60, 63, 67, 70, 73, 77, 80%, or more of the starting volume of body fluid placed into the body fluid reservoir. An example of anabolic therapeutic factors to catabolic fluid factors is IL-1ra to IL-1ß at a ratio ranging from substantially 10:1 to 1,000:1.

A feature of devices disclosed herein is that the devices can not only filter contaminants away from the desired therapeutic factors, but can also concentrate the therapeutic factors. The concentration of the therapeutic factors allows for an increased level of therapeutic factors over baseline levels in mammalian body fluid. The methods and devices disclosed herein can provide a concentration substantially 1, 2, 4, 5, 10, 50, 100, 250, 500, 750, 1,000 fold or more increase of the desired therapeutic factors in the therapeutic fluid over baseline levels (e.g., the starting body fluid). The methods and devices can also remove one or more therapeutic factors or contaminants from the therapeutic fluid. For example, there can be a substantially 1, 2, 4, 5, 10, 50, 100, 250, 500, 750, 1,000 fold or more decrease of undesired therapeutic factors or contaminants (cells, debris, proteins, tissue) in the therapeutic fluid over baseline levels (e.g., the starting body fluid). The methods and devices disclosed herein can provide substantially 0.1, 1.0, 2.0, 5.0, 10, 50, 100, 1,000, 2,000, 5,000 µg/mL or more increase of the desired therapeutic factors in the therapeutic fluid over baseline levels (e.g., the starting body fluid). The methods and devices can also remove one or more therapeutic factors or contaminants from the therapeutic fluid. For example, there can be substantially 0.1, 1.0, 2.0, 5.0, 10, 50, 100, 1,000, 2,000, 5,000 µg/mL or more decrease of undesired therapeutic factors or contaminants (cells, debris, proteins, tissue) in the therapeutic fluid over baseline levels (e.g., the starting body fluid).

Methods can include a step of withdrawing body fluid from a mammalian individual. The step of withdrawing body fluid from a mammal occurs before the placement of the body fluid into the body fluid reservoir of the apparatus. The withdrawing of body fluid can occur at the site of the apparatus and processing, or can occur off-site and the body fluid can be sent to the site of the apparatus for processing.

Definitions

Unless defined otherwise, all technical and scientific terms used herein have the same meaning as commonly understood to one of ordinary skill in the art. As used herein, the singular forms "a," "an," and "the" include plural referents unless the context clearly dictates otherwise. For example, reference to a "nucleic acid" means one or more nucleic acids.

It is noted that terms like "commonly" and "typically" are not utilized herein to limit the scope of the claimed devices or methods or to imply that certain features are critical, essential, or even important to the structure or function.

It is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the term "body fluid" refers to a biological fluid collected from a subject. The subject can be a mammal, including but not limited to human, equine, canine, feline, bovine, porcine, rodent, sheep, or goat. The body fluids can be autogenic, allogenic, or xenogenic. Body fluids include, but are not limited to, whole blood, plasma, serum, urine, saliva, mucus, cerebrospinal fluid, lymphatic fluid, seminal fluid, amniotic fluid, vitreous fluid, as well as fluid collected from cell culture of patient cells, and the like. Body fluids also include body fluids derived from tissue such as, for example, bone, bone marrow, muscle, brain, heart, liver, lung, stomach, small intestine, large intestine, colon, uterus ovary, testis, cartilage, soft tissue, skin, subcutaneous tissue, breast tissue, tissue obtained from other species, patient tissue from surgery, and the like. The tissue can be disrupted. Methods for disrupting tissue are known and include homogenization and enzymatic treatments. The body fluids also include, for example, bone marrow, fluids obtained from surgery, fluid filtrates, tissue filtrates or fragments, bone chips or fragments obtained during surgery, and the like.

The term "concentrated" refers to a fluid which has been separated by gravity, centrifugation, and/or filtration into various fractions. As used herein, the term "concentrated" is synonymous with the term "enriched," meaning increasing the proportion of desired therapeutic factors in the body fluid to produce a therapeutic fluid. The term "fraction" refers to the various components into which a biological fluid can be separated by centrifugation, gravitational weight separation and/or filtration. Every fraction can be enriched with a particular fluid component (i.e. concentrated) relative to the other fractions and the original fluid. The concentration process can remove one or more nonessential components from the bodily fluid. The concentration process can also remove nonessential components such that the concentrated fraction contains desired components.

The term "therapeutic fluid" means a body fluid that has been filtered and enriched with a higher concentration of one or more therapeutic factors than occurs in the starting body fluid. As used herein, "therapeutic factors" are components of mammalian body fluid that can be used as therapeutics, for example, growth factors, differentiation factors, chemotactic factors, adhesion molecules, anti-inflammatories, globulins, and other proteins that can be used as therapeutics such as interleukin-1 receptor antagonist (IL-1ra), thrombin and alpha-2 macroglobulin. Therapeutic fluid can also include, but is not limited to, blood fractions (platelet rich plasma (PRP), platelet poor plasma (PPP)), stem cells (cord blood-derived and bone marrow-derived) for example, concentrated seminal fluid, concentrated spinal fluid and the like.

As used herein, the term "autograft" refers to a body fluid, tissue, or organ obtained from a part of the patient's body and is placed back to the same patient's body. Autograft materials include, without limitation, bone, bone powder, bone chips, or bone particles, tendons, ligaments, cartilage, muscle, skin, lens fragments, and the like, obtained from mammalian sources, including, but not limited to, equine, canine, feline, bovine, porcine, rodent, sheep, or goat, and human sources.

"Allograft" as used herein refers to a body fluid, tissue, or organ obtained from one patient and grafted to a genetically dissimilar patient of the same species. Allograft materials include, without limitation, bone, bone powder, bone chips, or bone particles, tendons, ligaments, skin, cartilage, muscle, lens fragments, and the like, obtained from mammalian sources, including, but not limited to, equine, canine, and human sources. Human sources include patients and cadavers. Allograft materials can be freeze-dried and then must be reconstituted in a biocompatible fluid prior to use. Allograft materials can also be substituted or supplemented with biosynthetic and synthetic materials including, without limitation, demineralized bone matrix, collagen, ceramics, cements, polymers and copolymers. Allograft materials can be obtained from mammalian sources, including, but not limited to, equine, canine, feline, bovine, porcine, rodent, sheep, or goat, and human sources.

As used herein, the term "xenograft" refers to a tissue or organ obtained from one species and placed into an individual of another species. Xenograft materials include, without limitation, bone, bone powder, bone chips, or bone particles, tendons, ligaments, skin, cartilage, muscle, lens fragments, and the like, obtained from mammalian sources, including, but not limited to, equine, canine, and porcine. Xenograft materials can be freeze-dried and then must be reconstituted in a biocompatible fluid prior to use. Xenograft materials can be obtained from mammalian sources, including, but not limited to, equine, canine, feline, bovine, porcine, rodent, sheep, or goat, and human sources.

The term "growth factor" as used herein means a bioactive molecule that promotes proliferation of a cell or tissue. Useful growth factors include, but are not limited to, transforming growth factor-alpha (TGF-alpha), transforming growth factor-beta (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF and VEGF, for example, can promote growth and/or differentiation of a cell or tissue. Some growth factors include VEGF, NGFs, PDGF-AA, PDGF-BB, PDGF-AB, FGFb, FGFa, and BGF.

The term "differentiation factor" as used herein means a bioactive molecule that promotes differentiation of cells or tissue. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors can also promote growth or proliferation of a cell or tissue. TGF and IL-3, for example, can promote differentiation and/or growth of cells.

"Chemotactic factors" refers to a bioactive molecule responsible for regulating the movement of chemicals needed for proper development, healing and/or homeostasis of cells and tissues. Chemotactic factors include cytokines. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, TNF-beta, and IL-1ra.

The term "adhesion molecule" refers to bioactive molecules that promote or facilitate adhesion with other cells or with the extracellular matrix (ECM) or basement membrane (BM). Adhesive molecules include actin, fibrin, fibrinogen, fibronectin, vitronectin, laminin, cadherins, selectins, intracellular adhesion molecules 1, 2, and 3, and cell-matrix adhesion receptors including but not limited to integrins such as $\alpha 5\beta 1$, $\alpha 6\beta 1$, $\alpha 7\beta 1$, $\alpha 1\beta 2$, $\alpha 2\beta 3$, and $\alpha 6\beta 4$.

As used herein, the terms "treatment" and "treating" refer to the process of administering or applying a therapeutic fluid to a patient at the site of a wound or injury in order to cause or promote healing at the wound or injury site. The concentrated fluid can be autogenic, allogenic, or xenogenic. The concentrated therapeutic fluid or concentrated body fluid can be applied in a therapeutically effective amount. For example, an amount sufficient to cause wound or injury healing when a therapeutic fluid is applied to a wound or injury site would be a therapeutically effective amount.

The concentration of therapeutic factors can be detected, quantified, and/or analyzed by techniques generally available to one skilled in the art, for example, but not limited to, absorbance at 280 nm, enzyme-linked immunosorbent assay (ELISA), Bradford assay, and BCA assay.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z."

EXAMPLES

The examples that follow are illustrative of specific methods and devices disclosed herein and various uses thereof. They are set forth for explanatory purposes only, and are not to be taken as limiting.

Example 1

One exemplary composition comprises a concentrator apparatus where the top plate and bottom plate are permanently connected. The filter material comprises a porous polyethylsulfone material that is placed between the struts of the apparatus. The mammalian body fluid is placed into the fluid reservoir of the apparatus by way of a port that is sealed with a Leur Lock cap. The concentrator apparatus with the body fluid is incubated at substantially 37° C. for substantially 24 hours. Subsequent to the incubation, the apparatus with fluid is put into a centrifuge, such as, but not limited to, the Angel® centrifuge (Cytomedix) and centrifuged at 4,000×g for 10 minutes. After centrifugation, the device is removed from the centrifuge, the cap covering the port for the therapeutic fluid reservoir removed, and the therapeutic fluid removed from the device. The therapeutic fluid can then be used to treat a patient.

Example 2

One exemplary composition comprises a concentrator apparatus where the top plate and bottom plate can be separated. The filter material comprises a porous polyethylsulfone material that is placed between the struts of the apparatus. The mammalian body fluid is placed into the fluid reservoir of the apparatus by way of a port that is sealed with a Leur Lock cap. The concentrator apparatus with the body fluid is incubated at substantially 37° C. for substantially 24 hours. Subsequent to the incubation, the apparatus with fluid is put into a centrifuge, such as, but not limited to, the Angel® centrifuge (Cytomedix) and centrifuged at 4,000×g for 10 minutes. After centrifugation, the device is removed from the centrifuge, the cap covering the port for the therapeutic fluid reservoir removed, and the therapeutic fluid removed from the device. The therapeutic fluid can then be used to treat a patient.

Example 3

One exemplary composition comprises a concentrator apparatus where the top plate and bottom plate can be separated. The filter material comprises a porous polyethylsulfone material that is placed between the struts of the apparatus. The fluid reservoir of the concentrator apparatus comprises borosilicate beads. Mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid is put into a centrifuge, such as, but not limited to, the Angel® centrifuge (Cytomedix) and centrifuged at 4,000×g for 10 minutes. After centrifugation, the device is removed from the centrifuge, the cap covering the port for the therapeutic fluid reservoir removed, and the therapeutic fluid removed from the device. The therapeutic fluid can then be used to treat a patient.

Example 4

One exemplary composition comprises a concentrator apparatus where the top plate and bottom plate can be separated. The filter material comprises a porous polyethylsulfone material that is placed between the struts of the apparatus. The fluid reservoir of the concentrator apparatus comprises mammalian bone fragments. Mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid is put into a centrifuge, such as, but not limited to, the Angel® centrifuge (Cytomedix) and centrifuged at 4,000×g for 10 minutes. After centrifugation, the device is removed from the centrifuge, the cap covering the port for the therapeutic fluid reservoir removed, and the therapeutic fluid removed from the device. The therapeutic fluid can then be used to treat a patient.

Example 5

An exemplary composition comprises a concentrator apparatus where the top plate and bottom plate can be separated. The fluid reservoir of the concentrator apparatus comprises borosilicate beads. 100 mL of mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid and borosilicate beads is put into a centrifuge, such as, but not limited to, the Angel® centrifuge (Cytomedix) and centrifuged at 10,000×g for 15 minutes. The filter material comprises a porous polyethylsulfone material that is placed between the struts of the apparatus. The filter material comprises pore sizes of 50 kD. After centrifugation, the device is removed from the centrifuge, the cap covering the port for the therapeutic fluid reservoir removed, and the therapeutic fluid removed from the device. The therapeutic fluid can then be used to treat a patient.

Example 6

An exemplary composition comprises a concentrator apparatus where the top plate and bottom plate can be separated. The fluid reservoir of the concentrator apparatus comprises borosilicate beads. 100 mL of mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid and borosilicate beads is put into a centrifuge, such as, but not limited to, the Angel® centrifuge (Cytomedix) and centrifuged at 10,000×g for 15 minutes. The filter material comprises a porous polyethylsulfone material that is placed between the struts of the apparatus. The filter material comprises pore sizes of 300 kD. After centrifugation, the device is removed from the centrifuge, the cap covering the port for the therapeutic fluid reservoir removed, and the therapeutic fluid removed from the device. The therapeutic fluid can then be used to treat a patient.

Example 7

An exemplary composition comprises a concentrator apparatus where the top plate and bottom plate can be separated. The fluid reservoir of the concentrator apparatus comprises borosilicate beads. 100 mL of mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid and borosilicate beads is put into a centrifuge, such as, but not limited to, the Angel® centrifuge (Cytomedix) and centrifuged at 10,000×g for 15 minutes. The filter material comprises a porous polyethylsulfone material that is placed between the struts of the apparatus. The filter material comprises pore sizes of 500 kD. After centrifugation, the device is removed from the centrifuge, the cap covering the port for the therapeutic fluid reservoir removed, and the therapeutic fluid removed from the device. The therapeutic fluid can then be used to treat a patient.

Example 8

An exemplary composition comprises a concentrator apparatus where the top plate and bottom plate can be separated. The fluid reservoir of the concentrator apparatus comprises borosilicate beads. 100 mL of mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid and borosilicate beads is put into a centrifuge, such as, but not limited to, the Angel® centrifuge (Cytomedix) and centrifuged at 10,000×g for 15 minutes. The filter material comprises a porous polyethylsulfone material that is placed between the struts of the apparatus. The filter material comprises pore sizes of 1,000 kD. After centrifugation, the device is removed from the centrifuge, the cap covering the port for the therapeutic fluid reservoir removed, and the therapeutic fluid removed from the device. The therapeutic fluid can then be used to treat a patient.

Example 9

An exemplary composition comprises a concentrator apparatus where the top plate and bottom plate can be separated. The fluid reservoir of the concentrator apparatus comprises borosilicate beads. 100 mL of mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid and borosilicate beads is put into a centrifuge, such as, but not limited to, the Angel® centrifuge (Cytomedix) and centrifuged at 10,000×g for 15 minutes. The filter material comprises a porous polyethylsulfone material that is placed between the struts of the apparatus. The filter material comprises pore sizes of 0.2 microns. After centrifugation, the device is removed from the centrifuge, the cap covering the port for the therapeutic fluid reservoir removed, and the therapeutic fluid removed from the device. The therapeutic fluid can then be used to treat a patient.

Example 10

An exemplary composition comprises a concentrator apparatus where the top plate and bottom plate can be separated. The fluid reservoir of the concentrator apparatus comprises borosilicate beads. 100 mL of mammalian whole blood is placed into the fluid reservoir of the apparatus by way of a port that is sealed with a Leur Lock cap. The concentrator apparatus with the body fluid is incubated at substantially 37° C. for substantially 24 hours. After incubation, the entire apparatus with fluid and borosilicate beads is put into a centrifuge, such as, but not limited to, the Angel® centrifuge (Cytomedix) and centrifuged at 10,000×g for 15 minutes. The filter material comprises a porous polyethylsulfone material that is placed between the struts of the apparatus. The filter material comprises pore sizes of 0.45 microns. After centrifugation, the device is removed from the centrifuge, the cap covering the port for the therapeutic fluid reservoir removed, and the therapeutic fluid removed from the device. The therapeutic fluid can then be used to treat a patient.

Having described the methods and devices in detail and by reference to specific examples thereof, it will be apparent that modifications and variations are possible without departing from the scope of the methods and devices defined in the appended claims. More specifically, although some aspects of the methods and devices are identified herein as particularly advantageous, it is contemplated that the methods and compositions are not limited to these particular aspects.

What is claimed is:

1. A method of producing a therapeutic fluid from a mammalian body fluid, the method comprising the steps of:
   (a) adding the mammalian body fluid to a circular inner body fluid reservoir of a concentrator apparatus, wherein the concentrator apparatus comprises:
      (i) the circular inner body fluid reservoir;
      (ii) an effluent collection reservoir that encircles the circular inner body fluid reservoir; and
      (iii) at least one filter element or membrane between the circular inner body fluid reservoir and the effluent collection reservoir, wherein the at least one filter element or membrane is removable;
   (b) subjecting the concentrator apparatus to centrifugation; and
   (c) removing the therapeutic fluid from the effluent collection reservoir of the concentrator apparatus, wherein the therapeutic fluid has an increased concentration, amount, or both of therapeutic factors as compared to the mammalian body fluid.

2. The method of claim 1, wherein the concentrator apparatus is configured such that during centrifugation, the mammalian body fluid moves through the at least one filter element or membrane to enter the effluent collection reservoir.

3. The method of claim 1, wherein the step of centrifuging the concentrator apparatus comprises centrifuging at a gravitation force of 1×g to 600,000×g for 1 minute to 60 minutes.

4. The method of claim 1, wherein the concentrator apparatus further comprises a scaffold device within the inner body fluid reservoir and the method further comprises a step of incubating the mammalian body fluid in the inner body fluid reservoir to allow for expansion or increase in therapeutic factors, wherein the incubation step occurs after the step of adding the mammalian body fluid into the inner body fluid reservoir, but before the step of centrifuging the concentrator apparatus.

5. The method of claim 4, wherein the incubating step is performed at a temperature of 20° C. to 44° C.

6. The method of claim 4, wherein the scaffold device comprises one or more of beads, spheres, gels, wool, powder, granules, or particles.

7. The method of claim 4, wherein the scaffold device comprises allograft tissue, autograft tissue, or xenograft tissue.

8. The method of claim 4, wherein the therapeutic factors comprise Interleukin-1 receptor antagonist (IL-1ra), thrombin, fibrinogen, alpha-2 macroglobulin, or combinations thereof.

9. The method of claim 1, wherein the method further comprises a step of treating a patient with the therapeutic fluid removed from the effluent collection reservoir.

10. The method of claim 1, wherein the at least one filter element or membrane comprises pores.

11. The method of claim 1, wherein the at least one filter element or membrane comprises: (a) a network of one or more nanofibers, a nanofibrillar structure, glass, silicon, polymeric membranes, or combinations thereof, wherein the one or more nanofibers, a nanofibrillar structure, glass, silicon, polymeric membranes comprise macropores, nanopores, polymer scaffold, or combinations thereof; or (b) polyethersulfone, polyvinylidene fluoride, or mixed cellulose esters; or (c) combinations thereof.

12. The method of claim 1, wherein the concentrator apparatus further comprises:
   a disc having a top plate, a bottom plate, and an outside wall, wherein the top plate, bottom plate, and outside wall all have an inner surface and an outer surface; such that a compartment enclosed by the top plate, bottom plate, and outside wall is formed; wherein the at least one filter element or membrane is located inside the compartment and forms the circular inner body fluid reservoir surrounded by an inside edge of the at least one filter element or membrane; and an effluent collection reservoir located between an outside edge of the at least one filter element or membrane and an inner surface of the outside wall.

13. The method of claim 12, wherein the top plate of the concentrator apparatus comprises at least one filter element or membrane holder on the inner surface of the top plate, on the inner surface of the bottom plate, or both the inner surface of the top plate and the inner surface of the bottom plate.

14. The method of claim 12, wherein the top plate, bottom plate, or both the top and bottom plates are permanently attached to the outside wall of the concentrator apparatus.

15. The method of claim 12, wherein the top plate, bottom plate, or the top plate and bottom plate can be separated from the concentrator apparatus.

16. The method of claim 12, wherein the top plate, bottom plate, or both top plate and bottom plate comprise: (a) one or more ports leading to the circular inner body fluid reservoir; (b) one or more ports leading to the effluent collection reservoir; and (c) a sealing element on the one or more ports.

17. The method of claim 12, wherein the outer surface of the outside wall comprises attachment points for a centrifuge rotor, wherein the attachment points are in the form of notches, fingers, gear teeth, or cogs.

18. The method claim 12, wherein the inner surface of the top plate, the inner surface of the bottom plate, or both the inner surface of the top plate and the inner surface of the bottom plate comprise struts for holding the at least one filter element or membrane in place.

19. The method of claim 1, wherein the at least one filter element or membrane is circular in shape, continuous, and encircles the body fluid reservoir.

* * * * *